(12) United States Patent
Gotta et al.

(10) Patent No.: US 9,309,188 B2
(45) Date of Patent: Apr. 12, 2016

(54) METHOD FOR ALLYLATING AND VINYLATING ARYL, HETEROARYL, ALKYL, AND ALKENE HALOGENIDES USING TRANSITION METAL CATALYSIS

(75) Inventors: Matthias Gotta, Burscheid (DE); Bernd Wilhelm Lehnemann, Köln (DE); Waldemar Maximilian Czaplik, Burscheid (DE); Matthias Mayer, Mannheim (DE); Axel Jacobi Von Wangelin, Regensburg (DE)

(73) Assignee: Saitigo GmbH, Leverkusen (DE)

( * ) Notice: Subject to any disclaimer, the term of this patent is extended or adjusted under 35 U.S.C. 154(b) by 66 days.

(21) Appl. No.: 13/577,278

(22) PCT Filed: Feb. 1, 2011

(86) PCT No.: PCT/EP2011/051390
§ 371 (c)(1),
(2), (4) Date: Mar. 27, 2013

(87) PCT Pub. No.: WO2011/098375
PCT Pub. Date: Aug. 18, 2011

(65) Prior Publication Data
US 2013/0184485 A1    Jul. 18, 2013

(30) Foreign Application Priority Data
Feb. 9, 2010   (DE) .................. 10 2010 007 226

(51) Int. Cl.
| | |
|---|---|
| *C07B 37/04* | (2006.01) |
| *C07B 49/00* | (2006.01) |
| *C07C 1/32* | (2006.01) |
| *C07C 15/44* | (2006.01) |
| *C07C 43/205* | (2006.01) |
| *C07C 253/04* | (2006.01) |
| *C07C 17/263* | (2006.01) |
| *C07C 41/30* | (2006.01) |
| *C07C 67/343* | (2006.01) |
| *C07C 209/68* | (2006.01) |
| *C07C 253/30* | (2006.01) |
| *C07C 1/30* | (2006.01) |
| *C07C 17/26* | (2006.01) |
| *C07C 41/24* | (2006.01) |
| *C07C 209/74* | (2006.01) |

(52) U.S. Cl.
CPC ............. *C07C 253/04* (2013.01); *C07B 37/04* (2013.01); *C07B 49/00* (2013.01); *C07C 1/30* (2013.01); *C07C 1/326* (2013.01); *C07C 17/26* (2013.01); *C07C 17/2632* (2013.01); *C07C 41/24* (2013.01); *C07C 41/30* (2013.01); *C07C 67/343* (2013.01); *C07C 209/68* (2013.01); *C07C 209/74* (2013.01); *C07C 253/30* (2013.01); *C07C 2103/26* (2013.01); *C07C 2527/128* (2013.01); *C07C 2531/22* (2013.01)

(58) Field of Classification Search
USPC ..................................... 558/357, 359
See application file for complete search history.

(56) References Cited

U.S. PATENT DOCUMENTS

| | | | |
|---|---|---|---|
| 7,026,478 B2 * | 4/2006 | Furstner et al. ............... 544/216 |
| 7,384,580 B2 * | 6/2008 | Knochel et al. ........... 260/665 G |
| 7,387,751 B2 * | 6/2008 | Knochel et al. ........... 260/665 G |
| 7,781,599 B2 | 8/2010 | Nakamura et al. |
| 7,939,698 B2 | 5/2011 | Roberge et al. |
| 8,030,520 B2 * | 10/2011 | Sundermeier ........... C07B 37/04 564/305 |
| 2009/0247764 A1 * | 10/2009 | Sundermeier et al. ......... 546/348 |
| 2012/0046471 A1 * | 2/2012 | Sundermeier ........... C07B 37/04 546/348 |
| 2013/0324745 A1 * | 12/2013 | Gotta et al. .................... 549/434 |
| 2014/0303333 A1 * | 10/2014 | Shaver et al. ................. 526/147 |

FOREIGN PATENT DOCUMENTS

CN         101318896 A  * 12/2008

OTHER PUBLICATIONS

Mayer et al. Communications: Adv. Synth. Catal. 352, 2147-2152 (2010).*
Lu et al. Organic Letters, vol. 10(16) 3517-3520 (2008).*
European Search Report from International Application PCT/EP2011/051390 dated Aug. 17, 2011, two (2) pages.

(Continued)

Primary Examiner — Nyeemah A Grazier

(57) ABSTRACT

What is described is a process for preparing organic compounds of the general formula (I)

R—R'    (I)

by converting a corresponding compound of the general formula (II)

R—X    (II)

in which
X is fluorine, chlorine, bromine or iodine to an organomagnesium compound of the general formula (III)

$[M^+]_n[R_mMgX_kY_l]$    (III)

wherein compounds of the formula (III) are reacted with a compound of the general formula (IV)

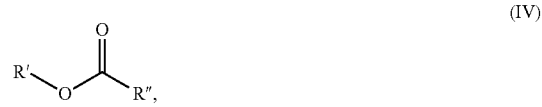

characterized in that the reaction of (III) with (IV) is performed in the presence of
a) catalytic amounts of an iron compound, based on the compound of the general formula (II), and optionally in the presence of
b) a nitrogen-, oxygen- and/or phosphorus-containing additive in a catalytic or stoichiometric amount, based on the compound of the general formula (II).

10 Claims, No Drawings

(56) References Cited

OTHER PUBLICATIONS

Karlstrom, et al. "Ferrocenyl Thiolates as Ligands in the Enantioselective Copper-Catalyzed Substitution of Allylic Acetates with Grignard Reagents", Xynlett 2001 SI, Thieme Stuttgart, New York, pp. 923-926.

Tamura et al., "Vinylation of Grignard Reagents, Catalysis by Iron", Journal of the American Chemical Society, 93:6, Mar. 24, 1971, pp. 1487-1489.

Wenkert et al., Transformation of Carbon-Oxygen into Carbon-Carbon Bonds Mediated by Low-Valent Nickel Species:, J. Org. Chem, 1984, 49 4894-4899.

Furstner et al., "Iron-Catalyzed Cross-Coupling Reactions of Alkyl-Grignard Reagents with Aryl Chlorides, Tosylates, and Triflates", Angew. Chem Int. Ed. 2002, 41 No. 4, Wiley-VCH VErlag GmbH, Weinheim Germany 2002, pp. 609-612.

Nakamura et al., "Iron-Catalyzed Cross-Coupling of Primary and Secondary Alkyl Halides with Aryl Grignard Reagents", J.Am. Chem Soc. 2004, 126 pp. 3686-3687.

Dohle et al., "Fe(III)-Catalyzed Cross-Coupling Between Functionalized Arylmagnesium Compounds and Alkenyl Halides", Synlett 2001, No. 12, 30 11 2001, Georg Thiem Verlag Stuttgart, New York, pp. 1901-1904.

Cahiez et al., "Iron-Catalyzed Alkylations of Aromatic Grignard Reagents", Angew. Chem, Int. Ed 2007, 46, Wiley-VCH Verlag GmbH & Co, Weinheim, Germany pp. 4364-4366.

Czaplik et al., "Domino Iron Catalysis: Direct Aryl-Alkyl Cross-Coupling", Angew, Chem. Int. Ed. 2009, 48, 2009 Wiley-VCH Verlag GmbH & Co, Weinheim, Germany, pp. 607-610.

Wenkert, et al. "Nickel-Induced Conversion of Carbon-Oxygen into Carbon-Carbon Bonds, One-Step Transformations of Enol Ethers into Olefins and Aryl Ethers into Biaryls", J. Am. Chem. Soc., 101:8, Apr. 11, 1979, pp. 2246-2247.

* cited by examiner

METHOD FOR ALLYLATING AND VINYLATING ARYL, HETEROARYL, ALKYL, AND ALKENE HALOGENIDES USING TRANSITION METAL CATALYSIS

The invention provides a process for preparing functionalized aryl, heteroaryl, alkenyl or alkyl compounds, by a transition metal-catalyzed cross-coupling reaction of an optionally substituted aryl, heteroaryl, alkenyl or alkylmagnesium compound with an optionally substituted allyl carboxylate, allyl carbonate, vinyl carboxylate or vinyl carbonate, wherein the formation of the organomagnesium compound from a halide can optionally proceed in situ, in parallel to the coupling reaction.

Transition metal-catalyzed cross-couplings are some of the most important synthetic tools in modern organic chemistry. The majority of the known cross-coupling reactions use palladium or nickel complexes as transition metal catalysts; in the case of coupling of allylic esters as coupling components with organomagnesium compounds, copper complexes are regularly the catalyst of choice (for example Karlström et al., Synlett 2001, 923), the prototype of which is the Kochi catalyst Li$_2$CuCl$_4$ (Tamura et al., Synthesis 1971, 303). The very rare literature descriptions of the coupling of vinyl esters with organomagnesium compounds involve exclusively nickel catalysis (for example Wenkert et al., J. Am Chem. Soc. 1979, 101, 2246 and J. Org. Chem. 1984, 49, 4894). Usually, in these couplings, organic ligands in the form of phosphines or N-heterocyclic carbenes are used, in order to achieve acceptable reactivity of the catalyst system. For economic (high palladium prices and high volatility of the palladium prices, costly ligands which are frequently unrecoverable) and toxicological reasons (high toxicity of nickel compounds and microbicidal action of copper ions in treatment plants), the use of these catalysts has distinct disadvantages. It would therefore be desirable to be able to use, for this reaction type, catalysts based on less expensive, readily available and non-toxic metals, if at all possible without expensive ligands which are difficult to prepare.

Under particular reaction conditions, iron compounds and also cobalt compounds also have activity as catalysts in cross-coupling reactions. Especially compounds of iron are available at very favorable prices in its capacity as a base metal, and are of no concern in terms of toxicology and wastewater legislation. Therefore, these compounds are preferable as catalyst systems to palladium, which is expensive, nickel, which is toxic and harmful to the environment, and copper, which is harmful to the environment.

As early as the early 1970s, it was shown that iron salts can catalyze the cross-coupling of vinyl halides with alkyl Grignard compounds (Kochi et al., J. Am. Chem. Soc. 1971, 1487). Due to a small range of application, this reaction found only very limited use over the next 30 years, until Knochel, Fürstner, Cahiez and Nakamura, since the start of the decade, succeeded in applying iron-catalyzed cross-couplings to a wider range of substrates with the aid of nitrogen-containing addition, for example N-methylpyrrolidone or N,N,N',N'-tetramethylethylenediamine (TMEDA) (for example Fürstner et al., Angew. Chem. Int. Ed. 2002, 41, 609; Nakamura et al., J. Am, Chem. Soc. 2004, 3686; Knochel et al., Synlett 2001, 1901; Cahiez et al., Angew. Chem. Int. Ed. 2007, 4364). These reactions are notable for particularly mild reaction conditions (−20° C. to +35° C.), high functional group compatibility (for example methyl esters, amines) and short reaction times (generally less than two hours). These reactions are also of particular interest for industrial application in that they generally do not require any expensive and sensitive phosphine or carbene ligands, as is frequently the case with nickel and palladium, especially when inexpensive chlorides rather than bromides or iodides are to serve as coupling partners.

A common feature of all these reactions is that they couple a Grignard compound to an alkyl, alkenyl or aryl halide, while it has not been possible to date to couple the widespread structural motif of the allyl function with these inexpensive and environmentally friendly catalysts. This appears to be at least partly because of the competing Kharasch reaction, which leads to the decomposition of the Grignard compound (cf. Fürstner et al., Angew. Chem. Int. Ed. 2002, 41, 609).

It was therefore an object of the present invention to find a process for preparing allyl and vinyl derivatives by cross-coupling, in which inexpensive and environmentally friendly catalysts can be used in order to couple readily available allyl and vinyl derivatives to aryl, heteroaryl, alkyl and alkenyl halides.

This object is achieved by the present invention by provision of a process which couples organomagnesium compounds derived from aryl, heteroaryl, alkyl and alkenyl halides, which can optionally be prepared in the presence of the allylic or vinylic coupling component, under catalysis by iron complexes, with allyl and vinyl carboxylates and allyl and vinyl carbonates, while maintaining the typical gentle conditions of iron catalysis. This allows the substrate range of the iron-catalyzed coupling to be widened considerably, since vinyl esters are obtainable in a very simple manner from aldehydes and ketones by enolization and acylation, and allyl esters from allyl alcohols.

The invention therefore provides a process for preparing organic compounds of the general formula (I)

in which

R is an optionally mono- or polysubstituted aryl, heteroaryl, alkenyl or alkyl radical, and R' is a vinyl or alkyl radical of the general formula II(a) or II(b)

where j is 0, 1, 2 or 3 and q are identical or different groups other than H, by converting a compound of the general formula (II)

in which

X is fluorine, chlorine, bromine or iodine, and

R is as defined for formula (I), to an organomagnesium compound of the general formula (III)

in which

R is as defined for formula (I),

X is an anion as defined for formula (II),

M is a monovalent cation,

Y is a monovalent anion, n is either 0 or n is 1, 2, 3, 4,
m is 1, 2, 3, 4, 5 or 6,
k is 0, 1, 2, 3 or 4,
l is 0, 1, 2, 3 or 4,
and, at the same time, the following relationship applies:

$n+2=m+k+1$, followed by reaction of the compound (III) with a compound of the general formula (IV)

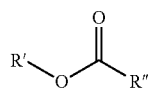

(IV)

in which
R' is as defined for formula (I) and is bonded to the oxygen atom in the allyl or vinyl position and
R" is an optionally substituted alkyl, alkoxy, aryl, aryloxy, heteroaryl or heteroaryloxy group,
characterized in that the reaction of (III) with (IV), and optionally also the step from (II) to (III), is performed in the presence of
a) catalytic amounts of an iron compound, based on the compound of the general formula (II),
and optionally in the presence of
b) a nitrogen-, oxygen- and/or phosphorus-containing additive in a catalytic or stoichiometric amount, based on the compound of the general formula (II).

The organomagnesium compound (III) can be prepared in a manner familiar to the person skilled in the art, for example by Grignard reaction of the compound (II) with elemental magnesium, and under suitable conditions also by halogen-metal exchange or deprotonation, optionally with addition of auxiliaries, for example lithium chloride, or by transmetalation of other organometallic compounds, e.g. organolithium compounds, with suitable magnesium compounds, e.g. magnesium salts or Grignard compounds. It is particularly advantageous to perform the preparation of the compound (III) by Grignard reaction in the presence of an iron compound which is capable of catalyzing both this reaction and the coupling of (III) with (IV) (domino catalysis; cf. Jacobi von Wangelin et al., Angew. Chem. Int. Ed. 2009, 48, 607). In this case, it is also possible to allow both the reaction of (II) to give (III) and the further reaction of (III) and (IV) to give (I) to proceed in parallel, i.e. to perform the preparation of (III) in the presence of the compound (IV), as a result of which the compound (III) formed in situ reacts immediately with compound (IV) to give the compound (I). In this case, it is possible to dispense with the isolation and/or storage of a potentially pyrophoric Grignard solution, which is thus difficult to handle under industrial conditions.

Examples of suitable organomagnesium compounds (III) are 4-tolylmagnesium chloride, undecylmagnesium bromide, bis(4-tolyl)magnesium, bis(4-methoxyphenyl)magnesium-lithium chloride complex, 2-methoxyphenylmagnesium chloride-lithium chloride complex, lithium tributylmagnesate, lithium dibutyl-(3-tolyl)magnesate or lithium tris(thiophen-2-yl)magnesate.

The R radical in the formulae (I), (II) and (III) is an optionally substituted $(C_1-C_{10})$-alkyl, $(C_2-C_{10})$-alkenyl, $(C_6-C_{24})$-aryl radical or heteroaryl radical, where the heteroaromatic radical is a five-, six- or seven-membered ring having one or more nitrogen, phosphorus, oxygen or sulfur atoms in the ring. Aromatic, heteroaromatic and/or cycloaliphatic rings may optionally be fused onto cyclic radicals.

Examples of preferred aromatic R radicals are optionally mono- or polysubstituted phenyl, naphthyl, anthracenyl or phenanthryl radicals. Examples of preferred heteroaromatic radicals are optionally mono- or polysubstituted pyridyl, pyrimidyl, pyrazinyl, furyl, thiophenyl, oxazolyl, thiazolyl or pyrrolyl radicals. Preferred alkenylic radicals are optionally mono- or polysubstituted vinyl radicals. Preferred alkylic radicals are optionally mono- or polysubstituted open-chain, cyclic, straight-chain or branched alkyl radicals, especially $C_1-C_{25}$-alkyl radicals.

The alkenylic, alkylic, aromatic or heteroaromatic R radical may optionally bear one or more substituents which may each independently be $(C_1-C_{18})$-alkyl, $(C_6-C_{18})$-cycloalkyl, $(C_3-C_{18})$-alkenyl, $(C_4-C_{18})$-cycloalkenyl, $(C_4-C_{18})$-alkynyl, $(C_4-C_{18})$-aryl, O—[$(C_4-C_{18})$-alkyl], O—[$(C_4-C_{18})$-aryl], O—Si[$(C_4-C_{18})$-alkyl]$_n$[$(C_4-C_{18})$-aryl]$_{3-n}$, OC(O)—[$(C_4-C_{18})$-alkyl], OC(O)—[$(C_4-C_{18})$-aryl], NH$_2$, NH[$(C_4-C_{18})$-alkyl], N[$(C_4-C_{18})$-alkyl]$_2$, NH[$(C_4-C_{18})$-aryl], N[$(C_4-C_{18})$-aryl]$_2$, NHC(O)—[$(C_4-C_{18})$-alkyl], N[$(C_4-C_{18})$-alkyl]C(O)—[$(C_4-C_{18})$-alkyl], NHC(O)—[$(C_4-C_{18})$-aryl], N[$(C_4-C_{18})$-alkyl]C(O)—[$(C_4-C_{18})$-aryl], NO$_2$, NO, S—[$(C_4-C_{18})$-aryl], S—[$(C_4-C_{18})$-alkyl], fluorine, chlorine, bromine, CF$_3$, CN, COOM, COO—[$(C_4-C_{18})$-alkyl], COO—[$(C_4-C_{18})$-aryl], C(O)NH—[$(C_4-C_{18})$-alkyl], C(O)NH—[$(C_4-C_{18})$-aryl], C(O)N—[$(C_4-C_{18})$-alkyl]$_2$, C(O)N—[$(C_4-C_{18})$-aryl]$_2$, CHO, SO$_2$—[$(C_4-C_{18})$-alkyl], SO—[$(C_4-C_{18})$-alkyl], SO$_2$—[$(C_4-C_{18})$-aryl], SO—[$(C_4-C_{18})$-aryl], OSO$_2$—[$(C_4-C_{18})$-alkyl], OSO$_2$—[$(C_4-C_{18})$-aryl], PO—[$(C_4-C_{18})$-alkyl]$_2$, PO—[$(C_4-C_{18})$-aryl]$_2$, SO$_3$M, SO$_3$—[$(C_4-C_{18})$-alkyl], SO$_3$—[$(C_4-C_{18})$-aryl] or Si[$(C_4-C_{18})$-alkyl]$_n$[$(C_4-C_{18})$-aryl]$_{3-n}$, where M is an alkali metal or alkaline earth metal atom and n is a natural number in the range from 0 to 3. In addition, two or more of these substituents may be joined to one another to form rings or ring systems.

Examples of preferred aromatic R radicals are 2-tolyl, 4-anisyl, 2-naphthyl, 4,4'-biphenyl, 3-tert-butoxycarbonylphenyl, 3,4-(2,2-difluoromethylenedioxy)phenyl, pentafluorophenyl or 2-decalinyl radicals. Examples of preferred heteroaromatic R radicals are 4-trifluoromethylpyridyl, 4-quinolinyl, 3-methoxythiophen-2-yl, 4-(2,2-ethylenedioxy)methylfuryl radicals. Examples of preferred vinylic R radicals are 2-methylprop-1-enyl, □-styryl, cyclohex-1-enyl, 2-chlorobut-1-enyl, 3-squalenyl or but-2-en-2-yl radicals. Examples of alkyl radicals are isopropyl, 1-butyl, 2-butyl, cyclohexyl, 4-methoxycyclohexyl or perfluorobutyl radicals.

The allylic or vinylic R' radical in formula (I) and formula (IV) may optionally bear one or more substituents Q which may each independently be $(C_4-C_{18})$-alkyl, $(C_4-C_{18})$-cycloalkyl, $(C_4-C_{18})$-alkenyl, $(C_4-C_{18})$-cycloalkenyl, $(C_4-C_{18})$-alkynyl, $(C_4-C_{18})$-aryl, O—[$(C_4-C_{18})$-alkyl], O—[$(C_4-C_{18})$-aryl], O—Si[$(C_4-C_{18})$-alkyl]$_n$[$(C_4-C_{18})$-aryl]$_{3-n}$, OC(O)—[$(C_4-C_{18})$-alkyl], OC(O)—[$(C_4-C_{18})$-aryl], NH$_2$, NH[$(C_4-C_{18})$-alkyl], N[$(C_4-C_{18})$-alkyl]$_2$, NH[$(C_4-C_{18})$-aryl], N[$(C_4-C_{18})$-aryl]$_2$, NHC(O)—[$(C_4-C_{18})$-alkyl], N[$(C_4-C_{18})$-alkyl]C(O)—[$(C_4-C_{18})$-alkyl], NHC(O)—[$(C_4-C_{18})$-aryl], N[$(C_4-C_{18})$-alkyl]C(O)—[$(C_4-C_{18})$-aryl], NO$_2$, NO, S—[$(C_4-C_{18})$-aryl], S—[$(C_4-C_{18})$-alkyl], fluorine, chlorine, bromine, CF$_3$, CN, COOM, COO—[$(C_4-C_{18})$-alkyl], COO—[$(C_4-C_{18})$-aryl], C(O)NH—[$(C_4-C_{18})$-alkyl], C(O)NH—[$(C_4-C_{18})$-aryl], C(O)N—[$(C_4-C_{18})$-alkyl]$_2$, C(O)N—[$(C_4-C_{18})$-aryl]$_2$, CHO, SO$_2$—[$(C_4-C_{18})$-alkyl], SO—[$(C_4-C_{18})$-alkyl], SO$_2$—[$(C_4-C_{18})$-aryl], SO—[$(C_4-C_{18})$-aryl], OSO$_2$—[$(C_4-C_{18})$-alkyl], OSO$_2$—[$(C_4-C_{18})$-aryl], PO—[$(C_4-C_{18})$-alkyl]$_2$, PO—[$(C_4-C_{18})$-aryl]$_2$, SO$_3$M, SO$_3$—[$(C_4-C_{18})$-alkyl], SO$_3$—[$(C_4-C_{18})$-aryl] or Si[$(C_4-C_{18})$-alkyl]$_n$[$(C_4-C_{18})$-aryl]$_{3-n}$, where M is an alkali metal or alkaline earth metal atom and n is a natural number in the range from 0 to 3. In addition, two or more of these substituents may be joined to one another to form rings or ring systems.

Examples of preferred allylic R' radicals are linear, branched and cyclic, optionally substituted $(C_3-C_{18})$-1-alken-3-yls from the group of allyl, crotyl, methallyl, 1-methylallyl, cyclopent-1-en-3-yl and cyclohex-1-en-3-yl. Examples of preferred vinylic R' radicals are linear, branched and cyclic, optionally substituted $(C_3-C_{18})$-1-alken-1-yls from the group of vinyl, 1-propenyl, 2-methyl-1-propenyl, cyclopent-1-en-1-yl or cyclohex-1-en-1-yl.

Typically, the process is performed by reacting the halogen compounds of the formula (II) with magnesium turnings to give the Grignard compound, then adding the catalytic amount of an iron or cobalt compound and then slowly adding the allyl or vinyl compound of the formula (IV) dropwise and then continuing to stir the reaction mixture for a period of 2 to 4 hours. The purification of the product formed pursues typically by column chromatography on silica gel.

If the compound of the formula (IV) is allyl acetate, the reaction is effected with compounds of the formula (II) preferably from the group of 4-bromoanisole, bromobenzene, 4-bromoveratrole, 4-bromotoluene, 4-bromoanisole, 2-bromotoluene and 4-tert-butylbromobenzene.

Crotyl acetate as the compound of the formula (IV) can preferably be reacted with compounds of the formula (II) from the group of 4-bromoanisole and 1-bromo-4-tert-butylbenzene.

If the compound of the formula (IV) is 3-vinylallyl acetate, the reaction is preferably effected with compounds of the formula (II) from the group of 1-bromo-4-chlorobenzene, 1-bromo-4-fluorobenzene, 1-bromo-2,4-difluorobenzene, 2-bromoanisole, methyl 4-bromobenzoate, 4-bromoanisole, 1,3-dibromobenzene, 1,4-dibromine, 4-bromoveratrole, 4-bromoanisole, 4-bromotoluene, 4-tert-butylbromobenzene.

The R" radical in formula (IV) may optionally bear one or more substituents which may each independently be $(C_1-C_{18})$-alkyl, $(C_1-C_{18})$-cycloalkyl, $(C_1-C_{18})$-alkenyl, $(C_1-C_{18})$-cycloalkenyl, $(C_1-C_{18})$-alkynyl, $(C_1-C_{18})$-aryl, O—[$(C_1-C_{18})$-alkyl], O—[$(C_1-C_{18})$-aryl], O—Si[$(C_1-C_{18})$-alkyl]$_n$ [$(C_1-C_{18})$-aryl]$_{3-n}$, OC(O)—[$(C_1-C_{18})$-alkyl], OC(O)—[$(C_1-C_{18})$-aryl], NH$_2$, NH[$(C_1-C_{18})$-alkyl], N[$(C_1-C_{18})$-alkyl]$_2$, NH[$(C_1-C_{18})$-aryl], N[$(C_1-C_{18})$-aryl]$_2$, NHC(O)—[$(C_1-C_{18})$-alkyl], N[$(C_1-C_{18})$-alkyl]C(O)—[$(C_1-C_{18})$-alkyl], NHC(O)—[$(C_1-C_{18})$-aryl], N[$(C_1-C_{18})$-alkyl]C(O)—[$(C_1-C_{18})$-aryl], NO$_2$, NO, S—[$(C_1-C_{18})$-aryl], S—[$(C_1-C_{18})$-alkyl], fluorine, chlorine, bromine, CF$_3$, CN, COOM, COO—[$(C_1-C_{18})$-alkyl], COO—[$(C_1-C_{18})$-aryl], C(O)NH—[$(C_1-C_{18})$-alkyl], C(O)NH—[$(C_1-C_{18})$-aryl], C(O)N—[$(C_1-C_{18})$-alkyl]$_2$, C(O)N—[$(C_1-C_{18})$-aryl]$_2$, CHO, SO$_2$—[$(C_1-C_{18})$-alkyl], SO—[$(C_1-C_{18})$-alkyl], SO$_2$—[$(C_1-C_{18})$-aryl], SO—[$(C_1-C_{18})$-aryl], OSO$_2$—[$(C_1-C_{18})$-alkyl], OSO$_2$—[$(C_1-C_{18})$-aryl], PO—[$C_1-C_{18})$-alkyl]$_2$, PO—[$(C_1-C_{18})$-aryl]$_2$, SO$_3$M, SO$_3$—[$(C_1-C_{18})$-alkyl], SO$_3$—[$(C_1-C_{18})$-aryl] or Si[$(C_1-C_{18})$-alkyl]$_n$[$(C_1-C_{18})$-aryl]$_{3-n}$, where M is an alkali metal or alkaline earth metal atom and n is a natural number in the range from 0 to 3. In addition, two or more of these substituents may be joined to one another to form rings or ring systems.

Examples of the R" radical in formula (IV) are methyl, ethyl, propyl, isopropyl or phenyl, methoxy, ethoxy, propoxy, isopropoxy or phenoxy radicals.

Examples of compound (IV) are allyl acetate, crotyl propionate, methallyl dodecanoate, cyclohex-1-en-3-yl butanoate, allyl methyl carbonate, (hex-1-en-3-yl)phenyl carbonate, and also vinyl acetate, 1-propenyl acetate, 2-propenyl methyl carbonate, cyclohex-1-en-1-yl propionate.

The catalysts used are preferably transition metal compounds of group VIIIB of the Periodic Table. Particular preference is given to using iron or cobalt compounds, very particular preference being given to using iron compounds in any oxidation state, preferably the +2 and +3 oxidation states, for example iron(II) chloride, iron(III) chloride, iron(II) acetylacetonate, iron(II) acetylacetonate, iron(II) acetate, iron(III) acetate, iron(II) bromide, iron(III) bromide, iron(II) fluoride, iron(III) fluoride, iron(II) iodide, iron(III) iodide, iron(II) sulfate, iron(II) trifluoroacetate, iron(II) trifluoromethanesulfonate, iron(III) trifluoromethanesulfonate, iron(III) chloride-TMEDA complex.

The amount of catalyst used is preferably 0.01 to 100 mol %, more preferably 0.1 to 10 mol %, based on the compound of the general formula (II).

It is optionally possible in the process according to the invention to add nitrogen-, oxygen- and/or phosphorus-containing additives.

These additives are preferably alkylamines, cycloalkylamines, alkyldiamines, cycloalkyldiamines, N-containing heterocycles, alkylamides, cyclic alkylamides, alkylimines, aniline derivatives, ureas, urethanes, nitrogen-containing heteroaromatics, dialkyl ethers, alkyl aryl ethers, diaryl ethers, cyclic ethers, oligoethers, polyethers, triarylphosphines, trialkylphosphines, aryldialkylphosphines, alkyldiarylphosphines and bridged bisphosphines.

The additives used are more preferably triethylamine, ethyldiisopropylamine, N,N,N',N'-tetramethylethylenediamine (TMEDA), 1,4-diazabicyclo[2.2.2]octane (DABCO), sparteine, N,N,N',N'-tetramethyldiaminomethane, 1,2-diaminocyclohexane (DACH), N-methyl-2-pyrrolidine (NMP), N,N-dimethylaniline, pyridine, phenanthroline, PEG (polyethylene glycol), DME (1,2-dimethoxyethane), binaphthyl dimethyl ether, 18-crown-6, triphenylphosphine, tri-n-butylphosphine, tri-tert-butylphosphine, dppf (1,1'-bis (diphenylphosphino)ferrocene), dppe (1,2-bis (diphenylphosphino)ethane), dppp (1,3-bis (diphenylphosphino)propane), dppb (1,4-bis (diphenylphosphino)butane) or dppe (1,5-bis (diphenylphosphino)pentane).

It is also possible to use chiral additives in order to achieve chiral induction in the coupling reaction, if applicable.

In the process according to the invention, the nitrogen-, oxygen- and/or phosphorus-containing additive is used preferably in an amount of 0 to 200 mol %, more preferably 0 to 150 mol %, based on the compounds (II).

The process according to the invention is typically performed in dry aprotic polar solvents, which are preferably used in dry form. Particular preference is given to using tetrahydrofuran (THF), 2-methyltetrahydrofuran (2-methyl-THF), 1,4-dioxane, dimethylformamide (DMF), dimethylacetamide (DMAc), methyl tert-butyl ether (MTBE), diethyl ether, 1,2-dimethoxyethane (DME, glyme), diisopropyl ether (DIPE), dipropyl ether, dibutyl ether, cyclopentyl methyl ether, diethylene glycol dimethyl ether (diglyme), triethylene glycol dimethyl ether (triglyme), tetraethylene glycol dimethyl ether (tetraglyme), diethylene glycol dibutyl ether, dimethyl carbonate or N-methyl-2-pyrrolidone (NMP) as the solvent.

The reaction temperature in the process according to the invention is typically between −80° C. and +100° C., preferably between −40 and +60° C., more preferably between −15 and +45° C.

In the process according to the invention, it is possible to react a multitude of substituted and unsubstituted aryl, heteroaryl, alkyl and alkenyl halides with substituted and unsubstituted allyl and vinyl esters of substituted and unsubstituted carboxylic acids and carbonic acid. The coupling is effected in most cases predominantly at the carbon atom of the allyl or vinyl ester that bears the ester function, which means that isomerization and allyl shifts take place only to a minor degree, if at all.

The compounds prepared by the process according to the invention can be isolated and purified efficiently by conventional methods.

EXAMPLES

Example 1

Coupling of Allyl Acetate with 2-methoxyphenylmagnesium Bromide

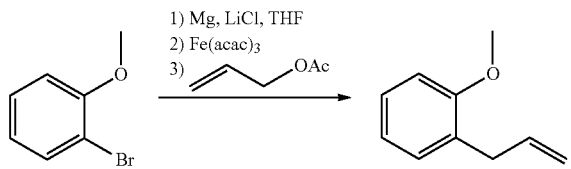

Under protective gas, 63 mg of magnesium turnings, 126 mg of anhydrous lithium chloride, 4 ml of dry tetrahydrofuran and 2.4 mmol of 2-bromoanisole were reacted at room temperature to give the Grignard compound. Then the dark-colored solution formed was cooled to 0° C. and a solution of 35.3 mg of iron(III) acetylacetonate (5 mol %) in 2 ml of dry tetrahydrofuran was added and the mixture was stirred for five minutes. Then 2 mmol of allyl acetate were added dropwise and the reaction mixture was stirred for 2 h. For workup, hydrolysis was effected with 5 ml of saturated sodium hydrogencarbonate solution and the mixture was extracted three times with 10 ml each time of ethyl acetate. The combined organic phases were dried over magnesium sulfate, concentrated and purified by column chromatography on silica gel (eluent: cyclohexane-ethyl acetate). 95% of theory of 2-allylanisole was isolated.

Examples 2 to 17

Further Couplings of Aryl Grignard Compounds with Allyl Acetate

The procedure was as in example 1, except that the haloarenes listed in table 1 were used instead of 2-bromoanisole. The individual yields are not optimized.

TABLE 1

| Example No. | Haloaromatic | Product | Yield (% of theory) |
|---|---|---|---|
| 2 | 4-bromoanisole | 4-allylanisole | 75 |
| 3 | bromobenzene | allylbenzene | 70 |
| 4 | 4-bromoveratrole | 4-allylveratrole | 72 |
| 5 | 4-bromotoluene | 4-allyltoluene | 75 |
| 6 | 1,3-dibromobenzene | 4-allylbromobenzene | 71 |
| 7 | 4-bromo-N,N-dimethylaniline | 4-allyl-N,N-dimethylaniline | 61 |
| 8 | 2-bromo-N,N-dimethylaniline | 2-allyl-N,N-dimethylaniline | 31 |
| 9 | 2-bromotoluene | 2-allyltoluene | 69 |
| 10 | 4-bromo-tert-butylbenzene | 4-allyl-tert-butylbenzene | 54 |
| 11 | 4-bromo-2-fluorobiphenyl | 4-allyl-2-fluorobiphenyl | 60 |

TABLE 1-continued

| Example No. | Haloaromatic | Product | Yield (% of theory) |
|---|---|---|---|
| 12 | 9-bromophenanthrene | 9-allylphenanthrene | 76 |
| 13 | 1,4-dibromobenzene | 4-allylbromobenzene | 35 |
| 14 | 2-bromobenzonitrile | 2-allylbenzonitrile | 15 |
| 15 | 1-bromo-4-fluorobenzene | 4-allylfluorobenzene | 75 |
| 16 | 4-bromobenzotrifluoride | 4-allylbenzotrifluoride | 51 |
| 17 | 5-bromo-m-xylene | 5-allyl-m-xylene | 63 |

Example 18

Coupling of an Alkyl Grignard Compound with Allyl Acetate

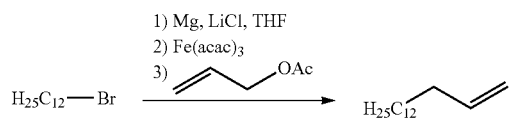

n-dodecyl bromide was converted analogously to example 1 to its Grignard compound and the latter was reacted with allyl acetate in the manner described. 1-Pentadecene was obtained in 32% yield.

Examples 19 to 23

Coupling of Aryl Grignard Compounds with Allyl Carbonate

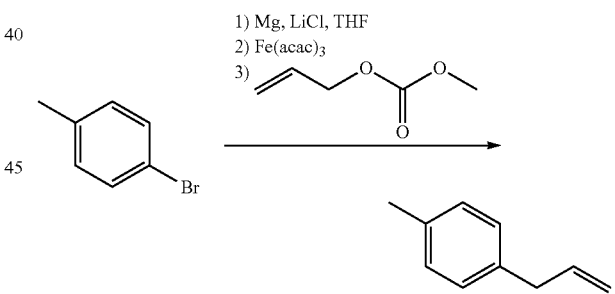

The experiments were conducted analogously to example 1; instead of allyl acetate, allyl methyl carbonate was used. The experiments are listed in table 2. The individual yields are not optimized.

TABLE 2

| Example No. | Haloarene | Product | Yield (% of theory) |
|---|---|---|---|
| 19 | 4-bromotoluene | 4-allyltoluene | 50 |
| 20 | 2-bromoanisole | 2-allylanisole | 76 |
| 21 | 4-bromoanisole | 4-allylanisole | 68 |
| 22 | 2-bromotoluene | 2-allyltoluene | 56 |
| 23 | 4-tert-butylbromobenzene | 4-allyl-tert-butylbenzene | 50 |

Examples 24 to 37

Coupling of Aryl Grignard Compounds with Substituted Allyl Acetates

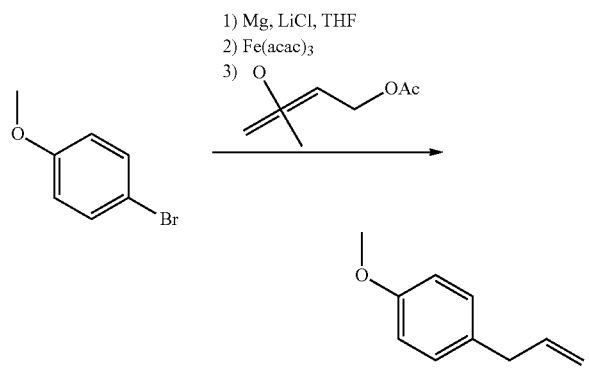

The experiments were conducted analogously to example 1; instead of allyl acetate, the substituted allyl acetates listed in table 3 were reacted with the aryl Grignard compounds listed. The individual yields were not optimized.

TABLE 3

| No. | Allyl compound | Haloarene | Product | Yield (%) |
|---|---|---|---|---|
| 24 | crotyl acetate | 4-bromoanisole | 4-crotylanisole | 30[a] |
| 25 | crotyl acetate | 1-bromo-4-tert-butylbenzene | 1-tert-butyl-4-crotylbenzene | 22[a] |
| 26 | 3-phenylallyl acetate | 1-bromo-4-chlorobenzene | 4-(3-phenylallyl)chlorobenzene | 94 |
| 27 | 3-phenylallyl acetate | 1-bromo-4-fluorobenzene | 4-(3-phenylallyl)fluorobenzene | 95 |
| 28 | 3-phenylallyl acetate | 1-bromo-2,4-difluorobenzene | 4-(3-phenylallyl)-m-difluorobenzene | 49 |
| 29 | 3-phenylallyl acetate | 2-bromoanisole | 2-allylanisole | 51 |
| 30 | 3-phenylallyl acetate | methyl 4-bromobenzoate | methyl 4-(3-phenylallyl)benzoate | 16 |
| 31 | 3-phenylallyl acetate | 4-bromoanisole | 4-(3-phenylallyl)anisole | 62 |
| 32 | 3-phenylallyl acetate | 1,3-dibromobenzene | 3-(3-phenylallyl)bromobenzene | 21 |
| 33 | 3-phenylallyl acetate | 1,4-dibromobenzene | 4-(3-phenylallyl)bromobenzene | 52 |
| 34 | 3-phenylallyl acetate | 4-bromoveratrole | 4-(3-phenylallyl)veratrole | 54 |
| 35 | prenyl acetate | 4-bromoanisole | 4-prenylanisole | 37[a] |
| 36 | prenyl acetate | 4-bromotoluene | 4-prenyltoluene | 35[a] |
| 37 | methyl 3-acetoxy-2-methylenebutanoate | 4-tert-butylbromobenzene | methyl 2-(4-tert-butylbenzylidene)butanoate | 41[a] |

[a] isomer mixture

Examples 38 to 40

Variation of the Coupling Temperature of the Allyl Acetate Coupling

Allyl acetate and 4-tert-butylphenylmagnesium bromide were reacted as described in example 10, except that the coupling reaction was conducted at the temperature listed in table 4.

TABLE 4

| No. | Temperature (° C.) | Yield (%) |
|---|---|---|
| 38 | 20 | 31 |
| 39 | 0 | 37 |
| 40 | −20 | 34 |

Examples 41 to 43

Variation of the Catalyst in the Allyl Acetate Coupling

Allyl acetate and 4-tert-butylphenylmagnesium bromide were reacted as described in example 10, except that the coupling reaction was conducted with the catalyst specified in table 5 (5 mol %).

TABLE 5

| No. | Catalyst | Yield (%) |
|---|---|---|
| 41 | iron(III) chloride | 37 |
| 42 | iron(III) acetylacetonate | 37 |
| 43 | iron(II) iodide | 7 |

Examples 44 to 47

Variation of the Stoichiometry in the Allyl Acetate Coupling

Allyl acetate and 4-tert-butylphenylmagnesium bromide were reacted as described in example 10, except that the stoichiometric ratios were varied as described in table 6.

TABLE 6

| No. | Molar bromoarene:allyl acetate ratio | Yield (%) |
|---|---|---|
| 44 | 1.0:1.2 | 33 |
| 45 | 1.0:1.5 | 37 |
| 46 | 1.2:1.0 | 40 |
| 47 | 1.5:1.0 | 51 |

Examples 48 to 52

Variation of Additives in the Allyl Acetate Coupling

Allyl acetate and 4-tert-butylphenylmagnesium bromide were reacted as described in example 10, except that the additives listed in table 7 were added in the amounts specified in each case.

TABLE 7

| No. | Eq. of LiCl | Eq. of TMEDA | Yield (%) |
|---|---|---|---|
| 48 | 1.5 | 0.0 | 47 |
| 49 | 1.5 | 0.4 | 44 |
| 50 | 1.5 | 0.9 | 39 |
| 51 | 1.5 | 1.5 | 37 |
| 52 | 0.0 | 0.0 | 37 |

Examples 53

Coupling of 4-tolylmagnesium Bromide with Vinyl Acetate

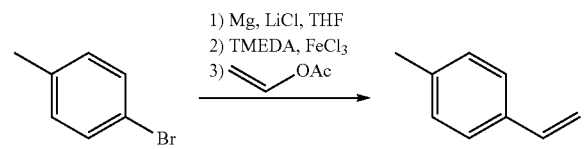

1) Mg, LiCl, THF
2) TMEDA, FeCl$_3$
3) ⟶OAc

Under protective gas, 96 mg of magnesium turnings were initially charged under 6 ml of a 0.5 M solution of lithium chloride in tetrahydrofuran. At 20° C., 2.6 mmol of 4-bromotoluene were added and the mixture was stirred for 2 h. A solution of 16.2 mg of iron(III) chloride (5 mol %) and 292 μl of TMEDA (1.3 eq.) in 1 ml of tetrahydrofuran was added to the Grignard solution formed. Then the mixture was cooled to 0° C. and 2 mmol of vinyl acetate were added, and the mixture was stirred at 0° C. for 3 h and at 20° C. for 1 h. For workup, 4 ml of saturated sodium carbonate solution were added and the mixture was extracted three times with 5 ml each time of ethyl acetate. The combined organic extracts were dried over sodium sulfate and purified by column chromatography on silica gel (eluent: cyclohexane-ethyl acetate).

This gave 4-methylstyrene in a yield of 99% of theory.

Example 54

Coupling of 4-bromoanisole with Vinyl Acetate

The reaction was conducted analogously to example 53, except using 4-bromoanisole instead of 4-bromotoluene. This gave 4-methoxystyrene in 100% yield.

Example 55

Coupling of Bromotoluene with Vinyl Acetate as Under Domino Iron Catalysis

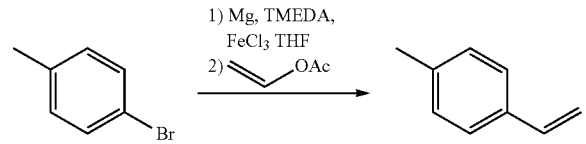

1) Mg, TMEDA, FeCl$_3$ THF
2) ⟶OAc

Under protective gas, 62 mg of magnesium turnings were initially charged under a solution of 16.2 mg (5 mol %) of iron(III) chloride in 6 ml of abs. tetrahydrofuran, and 60 tl of TMEDA (20 mol %) were added. The mixture was cooled to 0° C. and stirred for another 10 min, then 2.6 mmol of bromobenzene were added and the mixture was stirred at 0° C. for 90 mm, then 2 mmol of vinyl acetate were added and the mixture was stirred once again at 0° C. for 90 min. For workup, 2 ml of saturated sodium carbonate solution were added to the reaction mixture, which was extracted three times with 5 ml each time of ethyl acetate. The combined organic phases were dried over sodium sulfate, concentrated and purified by column chromatography on silica gel (eluent: cyclohexane-ethyl acetate).

This gave styrene in a yield of 42% of theory.

What is claimed is:

1. A process for preparing organic compounds of the general formula (I)

R—R'     (I)

in which
   R is an optionally mono- or polysubstituted aryl, heteroaryl, alkenyl or alkyl radical, and
   R' is an optionally substituted vinyl radical or ally radical, and
   the process comprises:
   converting a compound of the general formula (II)

R—X     (II)

in which
   X is fluorine, chlorine, bromine or iodine, and
   R is as defined for formula (I),
   to an organomagnesium compound of the general formula (III)

$[M^+]_n[R_mMgX_kY_l]$     (III)

in which
   R is as defined for formula (I),
   X is an anion as defined for formula (II),
   M is a monovalent cation,
   Y is a monovalent anion,
   n is either 0 or n is 1, 2, 3, 4,
   m is 1, 2, 3, 4, 5 or 6,
   k is 0, 1, 2, 3 or 4,
   l is 0, 1, 2, 3 or 4, and
   n+2=m+k+l, and
   reacting the organomagnesium compound (III) with a compound of the general formula (IV)

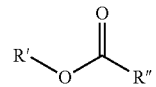     (IV)

in which
   R' is as defined for formula (I) and is bonded to the oxygen atom in the allyl or vinyl position, and
   R" is an optionally substituted alkyl, alkoxy, aryl, aryloxy, heteroaryl or heteroaryloxy group,
   to produce the compound of the general formula (I);
   wherein the process comprises converting compound (II) to compound (III) in the presence of
   a) catalytic amounts of an iron compound, based on the compound of the general formula (II),
   b) the compound of general formula (IV), and optionally
   c) a nitrogen-, oxygen- and/or phosphorus-containing additive in a catalytic or stoichiometric amount, based on the compound of the general formula (II);
   wherein, after formation of the organomagnesium compound (III), the organomagnesium compound (III) reacts further in situ with the compound of the general formula (IV) to produce the compound of the general formula (I).

2. The process according to claim 1, wherein R is an optionally substituted alkenyl, alkyl, aryl or heteroaryl radical, where the heteroaryl radical is a five-, six- or seven-membered ring having one or more nitrogen, oxygen and/or sulfur atoms in the ring, where any further optionally substituted aromatic, heteroaromatic and/or cycloaliphatic radicals may be fused onto a cyclic R radical and the R radical may optionally bear one or more substituents which may each independently be ($C_3$-$C_{18}$)-alkyl, ($C_3$-$C_{18}$)-cycloalkyl, ($C_3$-$C_{18}$)-alkenyl, ($C_3$-$C_{18}$)-cycloalkenyl, ($C_3$-$C_{18}$)-alkynyl, ($C_6$-$C_{18}$)-aryl, O—[($C_4$-$C_{18}$)-alkyl], O—[($C_6$-$C_{18}$)-aryl], O—Si[($C_4$-$C_{18}$)-alkyl]$_n$[($C_4$-$C_{18}$)-aryl]$_{3-n}$, OC(O)—[($C_4$-$C_{18}$)-alkyl], OC(O)—[($C_4$-$C_{18}$)-aryl], $NH_2$, NH[($C_4$-$C_{18}$)-alkyl], N[($C_4$-$C_{18}$)-alkyl]$_2$, NH[($C_4$-$C_{18}$)-aryl], N[($C_4$-$C_{18}$)-aryl]$_2$, NHC(O)—[($C_4$-$C_{18}$)-alkyl], N[($C_4$-$C_{18}$)-alkyl]C(O)—[($C_4$-$C_{18}$)-alkyl], NHC(O)—[($C_4$-$C_{18}$)-aryl], N[($C_4$-$C_{18}$)-alkyl]C(O)—[($C_4$-$C_{18}$)-aryl], $NO_2$, NO, S—[($C_4$-$C_{18}$)-aryl], S—[($C_4$-$C_{18}$)-alkyl], fluorine, chlorine, bromine, pentafluorosulfuranyl, $CF_3$, CN, COOM, COO [($C_4$-$C_{18}$)-alkyl], COO—[($C_4$-$C_{18}$)-aryl], C(O)NH—[($C_4$-$C_{18}$)-alkyl], C(O)NH—[($C_4$-$C_{18}$)-aryl], C(O)N—[($C_4$-$C_{18}$)-alkyl]$_2$, C(O)N—[($C_4$-$C_{18}$)-aryl]$_2$, CHO, $SO_2$—[($C_4$-$C_{18}$)-alkyl], SO—[($C_4$-$C_{18}$)-alkyl], $SO_2$—[($C_4$-$C_{18}$)-aryl], SO—[($C_4$-$C_{18}$)-aryl], $OSO_2$—[($C_4$-$C_{18}$)-alkyl], $OSO_2$—[($C_4$-$C_{18}$)-aryl], PO—[($C_4$-$C_{18}$)-alkyl]$_2$, PO—[($C_4$-$C_{18}$)-aryl]$_2$, $SO_3$M, $SO_3$—[($C_4$-$C_{18}$)-alkyl], $SO_3$—[($C_4$-$C_{18}$)-aryl] or Si[$C_4$-$C_{18}$)-alkyl]$_n$[($C_4$-$C_{18}$)-aryl]$_{3-n}$, where M is an alkali metal or alkaline earth metal atom and n is a natural number in the range from 0 to 3, and where at least two of these substituents may form a ring system with one another.

3. The process according to claim 1, wherein the one or more substituents Q may each independently be ($C_4$-$C_{18}$)-alkyl, ($C_4$-$C_{18}$)-cycloalkyl, ($C_4$-$C_{18}$)-alkenyl, ($C_4$-$C_{18}$)-cycloalkenyl, ($C_4$-$C_{18}$)-alkynyl, ($C_4$-$C_{18}$)-aryl, O—[($C_4$-$C_{18}$)-alkyl], O—[($C_4$-$C_{18}$)-aryl], O—Si[($C_4$-$C_{18}$)-alkyl]$_n$[($C_4$-$C_{18}$)-aryl]$_{3-n}$, OC(O)—[($C_4$-$C_{18}$)-alkyl], OC(O)—[($C_4$-$C_{18}$)-aryl], $NH_2$, NH[($C_4$-$C_{18}$)-alkyl], N[($C_4$-$C_{18}$)-alkyl]$_2$, NH[($C_4$-$C_{18}$)-aryl], N[($C_4$-$C_{18}$)-aryl]$_2$, NHC(O)—[($C_4$-$C_{18}$)-alkyl], N[($C_4$-$C_{18}$)-alkyl]C(O)—[($C_4$-$C_{18}$)-alkyl], NHC(O)—[($C_4$-$C_{18}$)-aryl], N[($C_4$-$C_{18}$)-alkyl]C(O)—[($C_4$-$C_{18}$)-aryl], $NO_2$, NO, S—[($C_4$-$C_{18}$)-aryl], S—[($C_4$-$C_{18}$)-alkyl], fluorine, chlorine, bromine, pentafluorosulfuranyl, $CF_3$, CN, COOM, COO—[($C_4$-$C_{18}$)-alkyl], COO—[($C_4$-$C_{18}$)-aryl], C(O)NH—[($C_4$-$C_{18}$)-alkyl], C(O)NH—[($C_4$-$C_{18}$)-aryl], C(O)N—[($C_4$-$C_{18}$)-alkyl]$_2$, C(O)N—[($C_4$-$C_{18}$)-aryl]$_2$, CHO, $SO_2$—[($C_4$-$C_{18}$)-alkyl], SO—[($C_4$-$C_{18}$)-alkyl], $SO_2$—[($C_4$-$C_{18}$)-aryl], SO—[($C_4$-$C_{18}$)-aryl], $OSO_2$—[($C_4$-$C_{18}$)-alkyl], $OSO_2$—[($C_4$-$C_{18}$)-aryl], PO—[($C_4$-$C_{18}$)-alkyl]$_2$, PO—[($C_4$-$C_{18}$)-aryl]$_2$, $SO_3$M, $SO_3$—[($C_4$-$C_{18}$)-alkyl], $SO_3$—[($C_4$-$C_{18}$)-aryl] or Si[($C_4$-$C_{18}$)-alkyl]$_n$[($C_4$-$C_{18}$)-aryl]$_{3-n}$, where M is an alkali metal or alkaline earth metal atom and n is a natural number in the range from 0 to 3, and where at least two of these substituents may form a ring system with one another.

4. The process according to claim 1 wherein the R" radical is an optionally branched, optionally cyclic alkyl group or an aryl or heteroaryl group, all of which may optionally bear one or more substituents which may each independently be ($C_1$-$C_{18}$)-alkyl, ($C_4$-$C_{18}$)-cycloalkyl, ($C_4$-$C_{18}$)-alkenyl, ($C_4$-$C_{18}$)-cycloalkenyl, ($C_4$-$C_{18}$)-alkynyl, ($C_4$-$C_{18}$)-aryl, O—[($C_4$-$C_{18}$)-alkyl], O—[($C_4$-$C_{18}$)-aryl], O—Si[($C_4$-$C_{18}$)-alkyl]$_n$[($C_4$-$C_{18}$)-aryl]$_{3-n}$, OC(O)—[($C_4$-$C_{18}$)-alkyl], OC(O)—[($C_4$-$C_{18}$)-aryl], $NH_2$, NH[($C_4$-$C_{18}$)-alkyl], N[($C_4$-$C_{18}$)-alkyl]$_2$, NH[($C_4$-$C_{18}$)-aryl], N[($C_4$-$C_{18}$)-aryl]$_2$, NHC(O)—[($C_4$-$C_{18}$)-alkyl], N[($C_4$-$C_{18}$)-alkyl]C(O)—[($C_4$-$C_{18}$)-alkyl], NHC(O)—[($C_4$-$C_{18}$)-aryl], N[($C_4$-$C_{18}$)-alkyl]C(O)—[($C_4$-$C_{18}$)-aryl], $NO_2$, NO, S—[($C_4$-$C_{18}$)-aryl], S—[($C_4$-$C_{18}$)-alkyl], fluorine, chlorine, bromine, pentafluorosulfuranyl, $CF_3$, CN, COOM, COO—[($C_4$-$C_{18}$)-alkyl], COO—[($C_4$-$C_{18}$)-aryl], C(O)NH—[($C_4$-$C_{18}$)-alkyl], C(O)NH—[($C_4$-$C_{18}$)-aryl], C(O)N—[($C_4$-$C_{18}$)-alkyl]$_2$, C(O)N—[($C_4$-$C_{18}$)-aryl]$_2$, CHO, $SO_2$—[($C_4$-$C_{18}$)-alkyl], SO—[($C_4$-$C_{18}$)-alkyl], $SO_2$—[($C_4$-$C_{18}$)-aryl], SO—[($C_4$-$C_{18}$)-aryl], $OSO_2$—[($C_4$-$C_{18}$)-alkyl], $OSO_2$—[($C_4$-$C_{18}$)-aryl], PO—[($C_4$-$C_{18}$)-alkyl]$_2$, PO—[($C_4$-$C_{18}$)-aryl]$_2$, $SO_3$M, $SO_3$—[($C_4$-$C_{18}$)-alkyl], $SO_3$—[($C_4$-$C_{18}$)-aryl] or Si[($C_4$-$C_{18}$)-alkyl]$_n$[($C_4$-$C_{18}$)-aryl]$_{3-n}$, where M is an alkali metal or alkaline earth metal atom and n is a natural number in the range from 0 to 3, and where at least two of these substituents may form a ring system with one another.

5. The process according to claim 1, wherein the iron compound is iron(II) chloride, iron(III) chloride, iron(II) acetylacetonate, iron(III) acetylacetonate, iron(II) acetate, iron(III) acetate, iron(II) bromide, iron(III) bromide, iron(II) fluoride, iron(III) fluoride, iron(II) iodide, iron(III) iodide, iron(II) sulfate, iron(II) trifluoroacetate, iron(II) trifluoromethanesulfonate, iron(III) trifluoromethanesulfonate or iron(III) chloride-TMEDA complex.

6. The process according to claim 1, wherein the iron compound is used in an amount of 0.01 to 50 mol %, based on the compound of the general formula (II).

7. The process according to claim 1, wherein the optionally added nitrogen-, oxygen- and/or phosphorus-containing additive having one or more nitrogen, oxygen and/or phosphorus atoms comprises optionally substituted alkylamines, N-containing heterocycles, alkylamides, cyclic alkylamides, cycloalkylamines, cycloalkyldiamines, alkylimines, cycloalkylimines, aniline, aniline derivatives, nitrogen-containing heteroaromatics, dialkyl ethers, alkyl aryl ethers, diaryl ethers, cyclic ethers, oligoethers, polyethers, triarylphosphines, trialkylphosphines, aryldialkylphosphines, alkyldiarylphosphines and bridged bisphosphines.

8. The according to claim 1, wherein the nitrogen-, oxygen- and/or phosphorus-containing additive used is triethylamine, ethyldiisopropylamine, N,N,N',N'-tetramethylethylenediamine (TMEDA), 1,4-diazabicyclo[2.2.2]octane (DABCO), sparteine, N,N,N',N'-tetramethyldiaminomethane, diaminocyclohexane (DACH), N-methyl-2-pyrrolidine (NMP), N,N-dimethylaniline, pyridine, phenanthroline, PEG-DME (polyethylene glycol dimethyl ether), DME (1,2-dimethoxyethane), binaphthyl dimethyl ether, 18-crown-6, triphenylphosphine, tri-n-butylphosphine, tri-tert-butylphosphine, dppf (1,1'-bis(diphenylphosphino)ferrocene), dppe (1,2-bis(diphenylphosphino)ethane), dppp (1,3-bis(diphenylphosphino)propane), dppb (1,4-bis(diphenylphosphino)butane) or dpppe (1,5-bis(diphenylphosphino)pentane).

9. The process according to claim 1, wherein the nitrogen-, oxygen- and/or phosphorus-containing additive is used in an amount of 0 to 200 mol %, based on the compound of the general formula (II).

10. The process according to claim 1, wherein:
the R radical in formula (I) is an aryl radical from the group of phenyl, naphthyl, anthracenyl, or phenanthryl, or a heteroaryl radical from the group of pyridyl, pyrimidyl, pyrazinyl, dioxinyl, furyl, (thiophen)yl, oxazolyl, isoxazolyl, thiazolyl, isothiazolyl, imidazolyl, pyrazolyl, oxadiazolyl, thiadiazolyl, triazolyl, or pyrrolyl, and
the R' radical in formula (I) is an allylic radical from the group of allyl, crotyl, methallyl, 1-methylallyl, cyclopent-1-en-3-yl, or cyclohex-1-en-3-yl, or a vinylic radical from the group of vinyl, 1-propenyl, 2-methyl-1-propenyl, cyclopent-1-en-1-yl, or cyclohex-1-en-1-yl.

* * * * *